(12) United States Patent
McCoy (10) Patent No.: US 9,669,997 B2
(45) Date of Patent: Jun. 6, 2017

(54) METHOD FOR DETERMINING THE PROFILE OF AN UNDERGROUND HYDROCARBON STORAGE CAVERN

(71) Applicant: James N. McCoy, Wichita Falls, TX (US)

(72) Inventor: James N. McCoy, Wichita Falls, TX (US)

(*) Notice: Subject to any disclaimer, the term of this patent is extended or adjusted under 35 U.S.C. 154(b) by 117 days.

(21) Appl. No.: 14/696,389

(22) Filed: Apr. 25, 2015

(65) Prior Publication Data

US 2016/0313166 A1 Oct. 27, 2016

(51) Int. Cl.
*G01F 17/00* (2006.01)
*B65G 5/00* (2006.01)

(52) U.S. Cl.
CPC ....................... *B65G 5/00* (2013.01)

(58) Field of Classification Search
CPC ................................. G01F 17/00; B65G 5/00
USPC ............................................................. 73/149
See application file for complete search history.

(56) References Cited

U.S. PATENT DOCUMENTS

| | | | |
|---|---|---|---|
| 2,772,564 A | 12/1956 | Dougherty | |
| 2,792,708 A * | 5/1957 | Johnston, Jr. ............ | B65G 5/00 73/149 |
| 3,049,920 A | 8/1962 | Allen | |
| 3,062,012 A | 11/1962 | Allen | |
| 4,408,676 A | 10/1983 | McCoy | |

(Continued)

FOREIGN PATENT DOCUMENTS

CN 100514018 C 12/2006

OTHER PUBLICATIONS

Berest P., Bergues J., Brouard B., Durup G., Guerber B., "A Tentative Evaluation of the MIT", Apr. 14 - 17, 1996, Houston SMRI Spring Meeting, Solution Mining Research Institute.

(Continued)

*Primary Examiner* — Monica S. Young
(74) *Attorney, Agent, or Firm* — Dale B. Nixon (57) ABSTRACT

Underground storage caverns are used for the bulk storage of hydrocarbon liquids, such as crude oil and gases, such as natural gas. The cavern is accessed through a bore hole which has casing and, for some bore holes, internal tubing with an annulus between the casing and tubing. The upper end of the cavern has a roughly cylindrical region termed the chimney. In order to check it for physical integrity, it is necessary to measure the profile of the chimney. This is also referred to as conducting a survey of the cavern. The cavern typically has hydrocarbon liquid above brine up to the surface. An inert gas can be injected above the hydrocarbon liquid to form an interface. The profile is conducted by driving the gas/liquid interface downward with gas pressure to a reference level determined by sequentially transmitting acoustic pulses to locate the reference level. Gas is injected to increase the pressure by a predetermined value and thereby drive down the interface by a known distance. The volume of the gas injected is used together with the known distance to determine a profile of the chimney. The process of injection of gas to increase the pressure by the predetermined value and measurement of the volume is repeated sequentially to determine the chimney profile at progressively lower regions, thereby producing an extended profile of the chimney.

12 Claims, 7 Drawing Sheets

(56) References Cited

U.S. PATENT DOCUMENTS

| | | | | |
|---|---|---|---|---|
| 4,455,869 | A | * | 6/1984 | Broussard ............ E21B 47/0003 405/53 |
| 4,474,053 | A | | 10/1984 | Butler |
| 4,624,130 | A | * | 11/1986 | Faul .................... E21B 47/0003 73/149 |
| 4,720,995 | A | * | 1/1988 | Thiel .................... G01F 17/00 73/149 |
| 5,117,399 | A | | 5/1992 | McCoy |
| 5,285,388 | A | * | 2/1994 | McCoy ................ E21B 47/042 367/113 |
| 6,874,361 | B1 | * | 4/2005 | Meltz .................... E21B 43/14 73/152.32 |
| 7,051,808 | B1 | * | 5/2006 | Vinegar ................ B09C 1/02 166/250.01 |
| 8,473,227 | B2 | * | 6/2013 | Olson .................... G01F 23/00 702/156 |
| 8,583,378 | B2 | * | 11/2013 | Jacques ................ E21B 49/008 166/250.02 |
| 8,902,704 | B2 | | 12/2014 | Zamow |
| 8,909,479 | B2 | | 12/2014 | Kvernvold |

OTHER PUBLICATIONS

Brouard B., Gerard D., "Tightness Tests in Salt-Cavern Wells", Spring 2002 Meeting Apr. 28-May 1, 2002, Banff, Alberta, Canada, Solution Mining Research Institute.

Bary A., Crotogino F., Prevedel B., Berger, H., Brown, K., Frantz, J., Sawyer, W., Henzell, M., Mohmeyer K., Ren N., Stiles K., Xiong H., "Storing Natural Gas Underground", Summer 2002, pp. 2-17, Oilfield Review.

Berest P., Brouard B., "Safety of Salt Caverns Used for Underground Storage", 2002, 8th Portuguese Congress for Geotechnique.

Berest P., Brouard B., "Safety of Salt Caverns Used for Underground Storage", vol. 58 (2003), No. 3, pp. 361-384, Oil and Gas Science and Technology—rev. IFP.

Brouard B., Karimi-Jafari M., Berest P., Durup G., "Pressure Build-Up in a Sealed Cavern: The effect of a Gas Blanket", Spring 2007 Conference, Apr. 2-May 2, 2007, Basel Switzerland, Solution Mining Research Institute.

Kansas Department of Health and Environment, "Nitrogen/Brine Interface Mechanical Integrity Test (MIT), Part I: Casing (Internal) MIT, Part II: Cavern (External) MIT", Jun. 6, 2011, Bureau of Water-Geology Section, Topeka, Kansas.

Brouard B., Berest P., Gillard P., "Set-Up of a Broken-Casings Detection System", SMRI Spring 2012 Technical Conference Apr. 23-24, 2012, Regina, Saskatchewan, Canada, Solution Mining Research Institute.

Brouard B., Berest P., Crabeil J., "Sounds Good? Determination of a Gas/Brine Interface by an Acoustic Method at Manosque", SMRI Fall 2012 Technical Conference, Oct. 1-2, 2012, Bremen, Germany, Solution Mining Research Institute.

\* cited by examiner

METHOD FOR DETERMINING THE PROFILE OF AN UNDERGROUND HYDROCARBON STORAGE CAVERN

CROSS REFERENCE TO RELATED APPLICATION(S)

Applicant has concurrently filed an application entitled "Method for Detecting Leakage in an Underground Hydrocarbon Storage Cavern" which has Ser. No. 14/696,387 and was filed on Apr. 25, 2015.

BACKGROUND

1. Field of the Invention

The present invention pertains to the field of underground storage caverns which are used for the bulk storage of liquid hydrocarbons, and in particular to the determination of the configuration of such caverns.

2. Description of the Related Art

In the use of underground storage caverns it is important to determine the approximate shape and volume of the cavern. This has heretofore been done by lowering a wireline device into the cavern and using sonic devices to measure distances from the device to the cavern wall. Another technique has been to pump a liquid into the annulus and determine cavern volume by measuring the liquid pressure and volume at the annulus and central tubing at the well surface. Wireline operations are complex, expensive and subject to leakage of gas or liquid from the wellhead or wireline connectors. Prior cavern survey techniques are shown in U.S. Pat. No. 2,792,708, issued May 21, 1957 entitled "Testing Underground Storage Cavities" and U.S. Pat. No. 3,049,920, issued Aug. 21, 1962 entitled "Method of Determining Amount of Fluid in Underground Storage".

BRIEF DESCRIPTION OF THE DRAWINGS

For a more complete understanding of the present invention and the advantages thereof, reference is now made to the following description taken in conjunction with the accompanying original drawings in which.

DETAILED DESCRIPTION OF THE INVENTION

Figure 1:
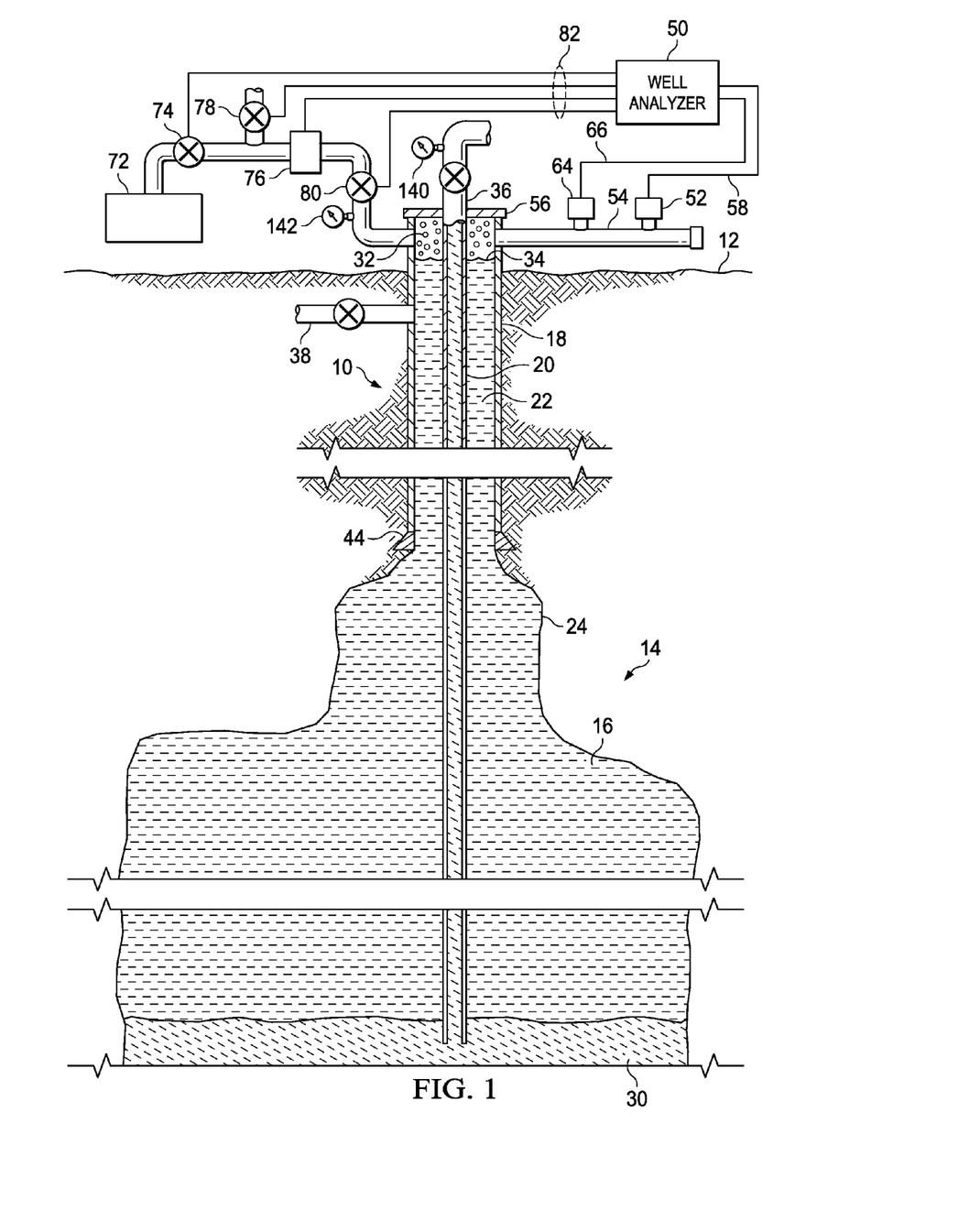
FIG. 1 is vertical section view of a hydrocarbon storage cavern together with casing, tubing and wellhead equipment.

Referring to FIG. 1, there is shown a well bore 10 which extends from the earth surface 12 down to an underground storage cavern 14. In this setting, the cavern 14 is used for the bulk storage of a liquid hydrocarbon 16 such as, for example, crude oil. Other liquid hydrocarbons include propane and butane. Within the well bore 10 there is a casing 18 at the outer perimeter and a string of tubing 20 positioned in the interior of the casing 18. Not all storage cavern bore holes include the tubing 20. The tubing 20 comprises interconnected tubing joints. The space between the tubing 20 and the casing 18 is termed an annulus 22. The annulus 22 is a generally circular open passageway which allows for the transmission of liquids and gasses.

The storage cavern is also referred to as a storage well.

The cavern 10 is typically produced in a salt formation by pumping water down through the tubing 20 to dissolve the salt and returning the resulting brine up through the annulus 22. Additional equipment is used to shape the cavern. This process is continued until a cavern 14 of useful volume is produced. Caverns can be produced which have the capacity to hold millions of barrels of liquid product. The upper end of the cavern 14 typically has a region termed a chimney 24. In this representation, the chimney can have a diameter of approximately 8 to 10 feet and a vertical length of 200 feet. The cavern 14 main chamber, as an example, can have a diameter of approximately two hundred feet and a vertical dimension of approximately 1,800 feet. The chimney could be located between 2,000 ft. and 2,200 ft. below the surface.

Such caverns are cost efficient and safe storage for volatile liquids and gasses, usually bulk hydrocarbons.

Further referring to FIG. 1, the cavern 14 has brine 30 at the bottom below the lighter liquid hydrocarbon 16. Typically, the liquid 16 fills the annulus 22. An inert gas 32, such as nitrogen, can be located above the liquid hydrocarbon 16 in the annulus 22 and chimney 24. The annulus 22 is typically filled to the surface with the liquid hydrocarbon 16. There can be a gas/liquid interface 34 at the surface of the liquid hydrocarbon 16 created by gas injection. Based on the volume of brine 30 and liquid hydrocarbon 16 in the annulus 22 and cavern 14, the interface 34 can be located in any one of the cavern 14, chimney 24 or annulus 22. The tubing 20 is typically filled with brine 30. The liquid hydrocarbon 16 is removed from the cavern 14 by pumping brine 30 down the tubing 20 thereby lifting the liquid hydrocarbon 16 and forcing it upward through the annulus 22 where it is directed through a pipeline 38 to storage tanks or a pipeline elsewhere, such as a refinery.

Still referring to FIG. 1, there is located at the lower end of the casing 18 a structure termed a casing shoe 44 which provides a transition from the lower end of the casing 18 to the interior surface of the chimney 24.

The apparatus used in conjunction with the present invention is shown in the upper portion of FIG. 1. An Echometer Company well analyzer 50, as shown at the site Echometer.com, is connected to activate a gas gun 52 which is mounted to pipe joints 54 for acoustic communication through the wellhead 56 to the annulus 22. Representative gas guns are the models "Compact Gas Gun", "Remote Fire Gas Gun", Wireless Remote Gas Gun", "5K PSI Gas Gun", and 15K PSI Gas Gun", all made and sold by Echometer Company. A representative gas gun is also shown in U.S. Pat. No. 4,408,676, entitled "Gas Gun Assembly" and issued Oct. 11, 1983, and which is incorporated by reference herein. The gas gun 52 can be manually activated or activated by the well analyzer 50 via a cable 58, or equivalent wireless link. The gas gun 52 includes a microphone for recording the sounds carried through the annulus 22. Sensors 64, for pressure and/or temperature, are connected to the well analyzer 50 via cable 66, or equivalent wireless link.

Acoustic sounding operation and apparatus are described in U.S. Pat. No. 5,285,388 entitled "Detection of Liquid Reflection for Echo Sounding Operation" issued Feb. 8, 1994 and U.S. Pat. No. 5,117,399 entitled "Data Processing and Display for Echo Sounding Data" issued May 26, 1992, both of which are incorporated herein by reference.

The gas gun 52 produces an acoustic (pressure) pulse which is transmitted through the pipe joints 54 to the annulus 22 and then downward toward the gas/liquid interface 34. The acoustic pulse reflects from striking the interface 34 and returns up the annulus 22 and through the pipe joints 54 to the microphone in the gas gun 52. The microphone receives acoustic energy of the reflected pulse and transmits it as a signal to the well analyzer 50. A gas gun 52 can generate either a positive (increasing pressure) pulse by using an externally supplied source of compressed gas, or can vent gas from the pipe joints 54, and thus from the annulus 22, to produce a negative (decreasing pressure) pulse.

For the present invention, the preferred acoustic pulse is a rarefaction pulse (negative) which creates a pressure pulse by a reduction in pressure. This is preferred because of the pressure that is present in the casing. The rarefaction pulse is produced by venting a small volume of gas from the casing. However, compression pulses can also be used. These compression pulses are produced by introducing gas at a higher pressure into the casing. This produces a pulse which has a pressure increase. Another type of pulse which can be used is a frequency shift pulse. This pulse has a changing frequency during the period of the pulse. A frequency shift pulse is detected by a process termed correlation, which produces a correlation pulse. The correlation pulse can have polarity that is a function of the relative area of the conduction path, such as the casing, and the interface surface, just as with rarefaction and compression pulses.

There is further used in conjunction with an embodiment of the invention, a nitrogen gas tank 72 that is connected through piping to a valve 74, a nitrogen gas mass flow meter assembly 76 and a valve 80 to the wellhead 56 into the annulus 22. A model of the meter in assembly 76 is the Micro Motion product Elite Coriolis meter. When the valves 74 and 80 are opened, either manually or electrically, nitrogen gas from the tank 72 flows through the meter assembly 76 and wellhead 56 into the annulus 22. A valve 78, when opened with valve 74 closed and valve 80 open, will vent nitrogen gas from the annulus 22 into the atmosphere, or be recovered and compressed. Piping is included in the meter assembly 76 to direct the gas flow direction as needed. The meter in assembly 76 fundamentally measures mass for the gas transmitted through it, and the mass measurement can be converted to standard gas volume.

The pressure in the tubing 20 is measured by a pressure meter 140. The pressure in the annulus 22 is measured by the pressure meter 142.

The valves 74, 78, and 80 and meter assembly 76 can optionally be electrically controlled by the well analyzer 50 through cables 82. They can also be operated manually.

Processes for operation of the invention are now described in reference to the Figures. Referring to FIG. 1, nitrogen gas is injected into the annulus 22. One step that can be used in the invention involves establishing a reference location for the gas/liquid interface 34.

Figure 2A:
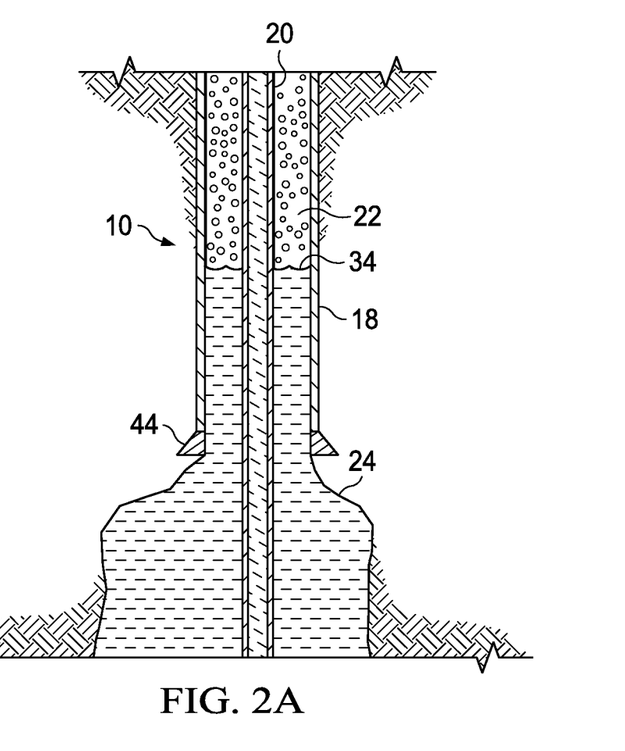
FIG. 2A is a partial section view of the cavern well bore shown in FIG. 1 showing a gas/liquid interface.
Figure 2B:
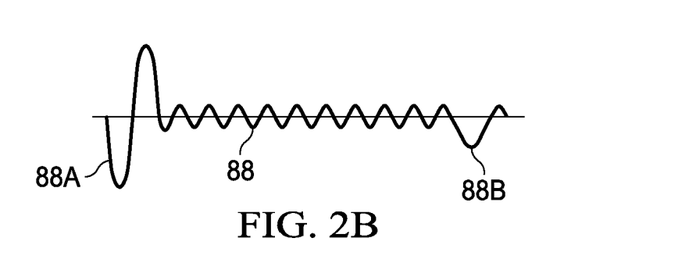
FIG. 2B is a waveform illustrating the signal monitored in the annulus at the surface as a result of an acoustic shot for the well illustration in FIG. 2A.

The first phase, injecting the nitrogen gas, is now described in reference to FIGS. 1, 2A, 2B, 3A, 3b, 4A, 4B and 9. The process begins with nitrogen gas injection into the annulus 22 from tank 72 via valve 74, meter assembly 76 and valve 80. During this first phase, the gas gun 52 is activated multiple times to produce acoustic shots. These can be at regular or irregular periods or at selected times. The initial shots are preferably rarefaction pulses produced by venting a small volume gas from the pressurized gas in the casing 18. Interface 34 is typically located in the annulus 22 near the surface 12 after a small volume of gas has been injected. As more nitrogen gas is injected into the annulus 22, the interface 34 is pushed downward. An acoustic shot signal 88 is shown in FIG. 2B taken when the interface 34 is located as shown in FIG. 2A. An initial pulse 88A is generated from the firing of the gas gun 52 and a reflection pulse 88B is returned after the pulse travels down to the interface 34, is reflected, and travels back to the microphone in the gas gun 52. For this embodiment of the invention, a negative going initial pulse indicates a rarefaction pulse which encounters a reduced annulus area, that is, the interface 34 reduces the annulus area to near zero. In FIG. 2B, the return has the same polarity as the initial pulse 88A, that is, negative going. Pulse 88B is not polarity inverted from pulse 88A.

Figure 3A:
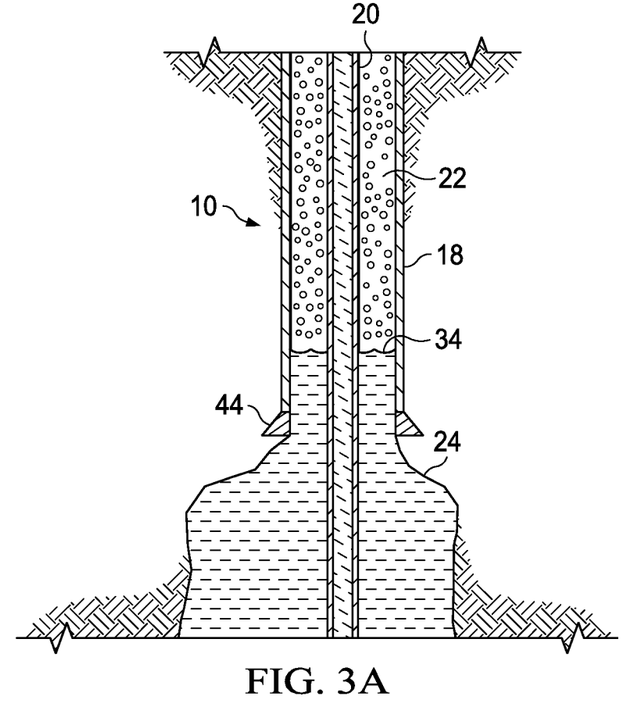
FIG. 3A is a partial section view of the cavern well bore shown in FIG. 1 showing a gas/liquid interface at a different level from that shown in FIG. 2A.
Figure 3B:
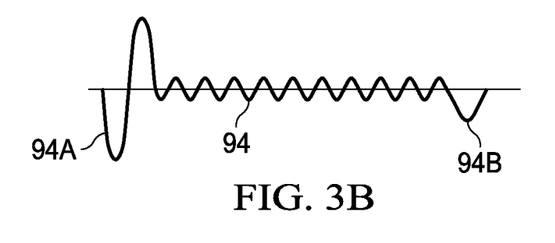
FIG. 3B is a waveform illustrating the signal monitored in the annulus at the surface as a result of an acoustic shot for the well illustration in FIG. A.

Continuing to FIGS. 3A and 3B, the interface 34 has been pushed further downward by an increasing amount of nitrogen gas injected into the well. An acoustic shot signal 94 is produced from a firing of the gas gun 52 to produce a rarefaction pulse 94A. The interface 34 is still within the annulus 22 so the reflection pulse 94B has the same polarity (negative going) as the initial pulse.

Figure 4A:
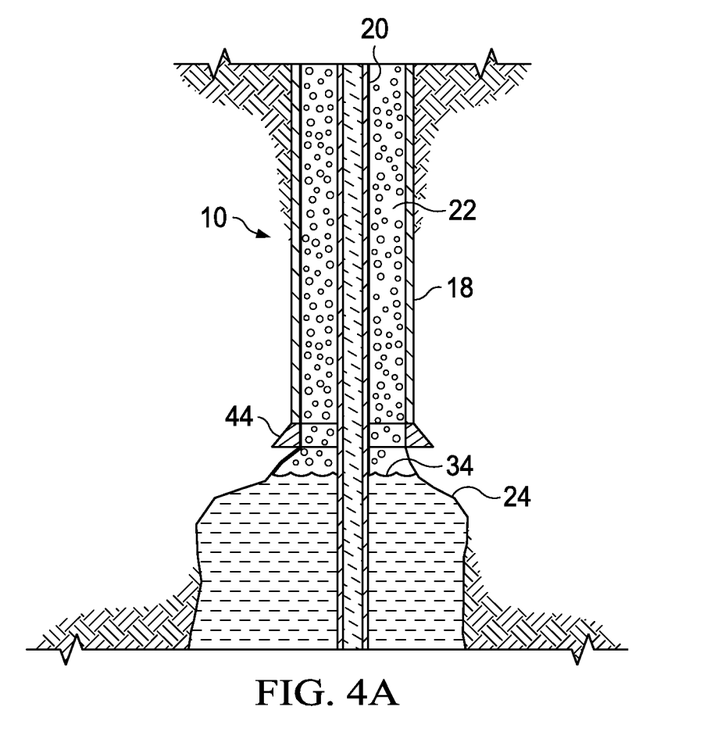
FIG. 4A is a partial section view of the cavern well bore shown in FIG. 1 showing a gas/liquid interface at just below the casing shoe level of the well.
Figure 4B:
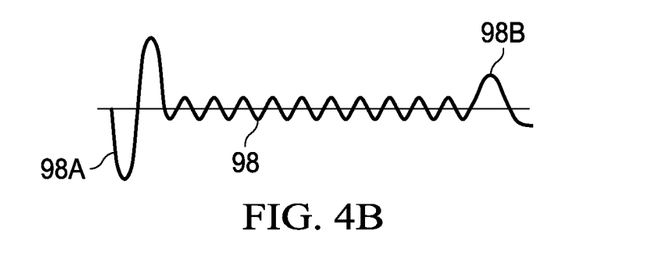
FIG. 4B is a waveform illustrating the signal monitored in the annulus at the surface as a result of an acoustic shot for the well illustration in FIG. 4A.

In FIG. 4A, the continuing flow, either steady or irregular, of nitrogen gas has pushed the interface 34 down to below the casing shoe 44 in the chimney 24, and is slightly below the lower end of the casing 18 and the casing shoe 44. This is typically in the range of 2 to 5 feet. The gas gun 52 produces a rarefaction shot which leads to the acoustic shot signal 98 (FIG. 4B) from the microphone in the gas gun 52. The initial shot is shown as pulse 98A. At this level, the surface area of the interface 34 is greater than that of the cross-sectional area of the annulus 22 within the casing 18. When the pulse encounters a sudden increase in area, as compared to that of the annulus, an inverted reflection is created. This increase in area produces an inverted reflection pulse 98B. This polarity inversion indicates that the gas/liquid interface 34 is located at a level in the chimney 24 just below the end of the casing 18. This level is used as a reference point, and it is not necessary to make a measurement of the actual depth to this level. This depth can be determined approximately by reference to the well log. The depth to the end of the casing 18 for a particular bore hole to a cavern is usually recorded in the well log that describes the details of the particular site. Thus, this record can provide the depth to the end of the casing string.

At the time that this polarity inversion is initially detected, the flow of nitrogen gas into the well is stopped. This location of the interface 34, as shown in FIG. 4A is termed the "reference level" for the interface 34. It is also referred to as a cross-sectional area transition level because the casing or annulus area is less than the cross-sectional area of the upper end of the chimney 24 immediately below the casing 18.

A parameter that is used in conjunction with the present invention is the gradient of the hydrocarbon liquid. This is expressed as psi/ft. The term "psi" is pounds per square inch. The gradient value can be determined by taking a sample of the hydrocarbon liquid, typically crude oil, at the surface from the annulus 22. This can be measured with a density instrument, such as a hydrometer, and from that measurement, the gradient can be calculated. A typical value for the gradient of crude oil is 0.33 psi/ft. Alternately, the liquid gradient can be determined by experimentation at the cavern test site. The gas pressure can be increased by a known amount and the change in the level of the interface can be measured using a device, for example an acoustic instrument such as the Echometer Company well analyzer. As an example, if the gas pressure in the annulus at the test site is increased by 33 psi and the column is measured to move down 100 ft., then the gradient is calculated as: Gradient=33/100=0.33.

Another technique for determining the gradient is to make a first pressure measurement when the interface 34 is at the top (the surface) of the casing 18. Inert gas is then injected into the casing 18 and acoustic shots taken, as described above, until the interface 34 reaches the reference level, which is a short distance below the lower end of the casing, just inside the top of the chimney 24. A second pressure measurement is taken with the interface 34 at the reference level. The depth of the reference is either known as a characteristic of the particular bore hole, or can be measured with acoustic sounding using the equipment described above. As an example, the casing pressure with the interface 34 at the surface could be 700 psi and when the interface 34 is pushed down to the reference level, the casing pressure, measured at the surface, could be 1,300 psi. The depth to the reference level is determined to be 2,100 ft. The gradient for this example is therefore: 600 psi/2,100 ft=0.29 psi/ft An embodiment of the invention is described in reference to FIG. 1, and the associated description, and with reference to FIGS. 5, 6, 7 and 8. The objective is to measure the approximate configuration of the chimney 24 and if needed, the configuration of the cavern 14. This can be referred to as a survey of the cavern. First, the interface 34 is pushed downward to just below the casing shoe 44 as described above to set it at the reference level. This reference level is known to be at the top of the chimney 24. In an example site, the nitrogen gas pressure, as measured at the surface by meter 142, is 1,500 psi, which is the pressure needed to push the interface 34 down to the reference level. From prior experimentation, it has been determined that a fixed increase in gas pressure depresses the interface 34 a fixed distance. This is the gradient for the hydrocarbon liquid. For a test cavern, an increase in pressure of 0.33 psi depresses the interface 34 by approximately 1 foot. This is a gradient value of 0.33 psi/ft. The standard volume of gas required to increase the pressure at the surface by this amount is measured by the meter 142. This volume of gas, adjusted for the pressure and temperature between the surface and at the level of the interface 34, establishes the approximate volume contained in a one foot high section of the chimney 24.

Figure 5:
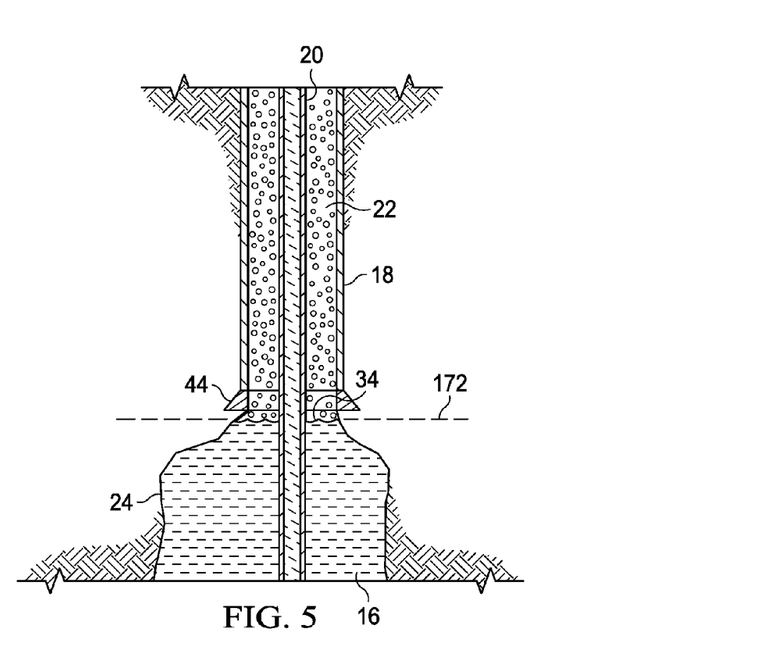
FIG. 5 is a section view of the lower end of the casing in a cavern well bore and the upper portion of the cavern chimney wherein the gas/liquid interface is located at just below the casing shoe of the cavern.

FIG. 5 illustrates the location of interface 34 at the top (reference level) of the chimney 24 and with a surface gas pressure of 1,500 psi. Line 172 represents the position of the interface 34.

Figure 6:
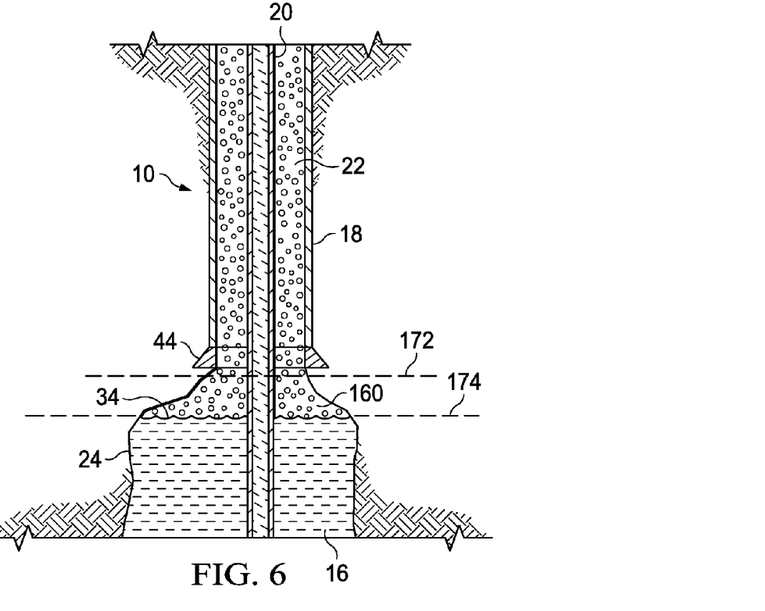
FIG. 6 is a section view of the lower end of the casing in a cavern well bore and the upper portion of the cavern chimney wherein the gas/liquid interface is located at a first depth below the casing shoe of the cavern.

In FIG. 6, the interface 34 has been pushed down approximate 1 foot by increasing the gas pressure to 1,500.3 psi to produce a region 160 within the chimney 24. Line 174 represents the position of interface 34 in this Figure. The space between lines 172 and 174 is a region 160. The volume of this region is related to the incremental volume of injected gas, with the necessary pressure and temperature compensation. Given the height (1 foot) and measured volume (V) and assumed generally cylindrical configuration, the width of the chimney at this level can be calculated. If the measured and compensated volume is 28 cubic feet, the height (h) is 1 foot and the assumed shape is cylindrical, the diameter (2R) of the chimney at this depth is approximately 6 feet. This is determined by the formula: $R^2=V/h\pi$ and D=2R Alternately, the volume can be divided by the incremental distance to determine an area for a given depth in the chimney 24. For this section, the volume is 23 ft$^3$ and the incremental distance is 1 ft., therefore the area at this depth is 23 ft$^2$.

Figure 7:
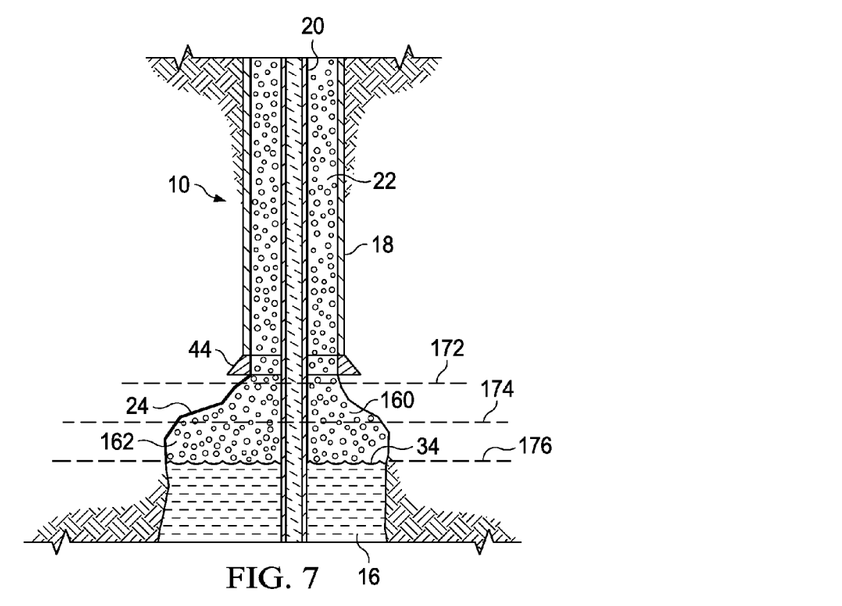
FIG. 7 is a section view of the lower end of the casing in a cavern well bore and the upper portion of the cavern chimney wherein the gas/liquid interface is located at a second depth below the casing shoe of the cavern.

Next the surface gas pressure is increased to 1,500.6 psi to depress the interface 34 downward another foot, as shown in FIG. 7, to the level represented by line 176. The space in the chimney 24 between lines 174 and 176 is a region 162. The same calculations and compensations are done to determine the diameter of the chimney 24 for region 162. This could be, for example, 6.5 feet.

Figure 8:
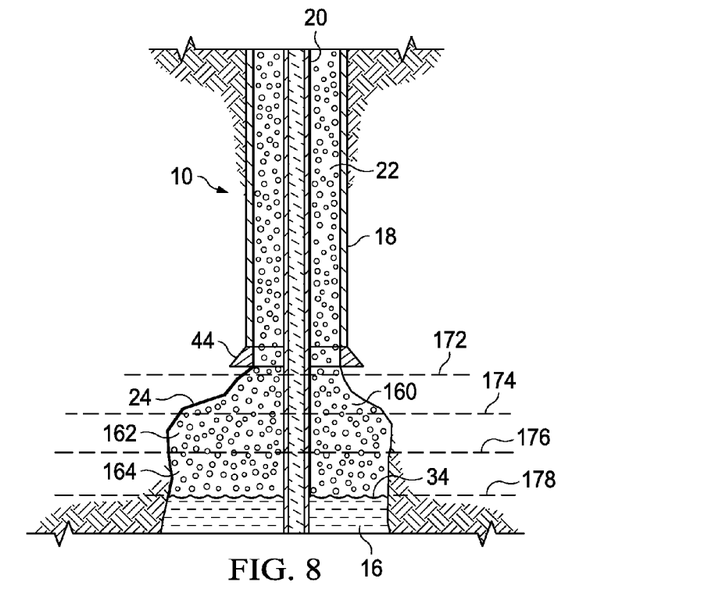
FIG. 8 is a section view of the lower end of the casing in a cavern well bore and the upper portion of the cavern chimney wherein the gas/liquid interface is located at a third depth below the casing shoe of the cavern.

The gas pressure is further increased to 1,500.9 psi to push down the interface 34 as shown in FIG. 8 to a level shown by line 178. The space in chimney 24 between lines 176 and 178 is a region 164. The diameter of the chimney in this region can be calculated as with the prior regions. It could be, for example, 6.7 feet. This process can be repeated for as deep into the chimney 24 as needed, and even going into the wider portion of cavern 14. The same calculation process is used in the cavern below the chimney. The steps are not limited to only one foot increments, for example, the pressure could be increased by 3.3 psi for a 10 foot depression.

The flow of inert gas into the casing described above can be continuous with continuous measurement of gas volume so that the parameters for calculating the profile can be produced, and plotted, at a continuous pace. For the processes using a release of gas, the flow can also be continuous with continuous monitoring of pressure and volume.

The gas standard volume measurements taken at the surface must be compensated to determine the gas volume in the well, such as in the chimney 24. This compensation includes changes in temperature and the weight of the gas column. Temperature profiles can be obtained from previously run temperature sampling for a specific cavern, be taken from standard temperature profiles for common fields or regions, or calculated based on models using the known physical aspects of a cavern, such as location, depth, earth strata and adjacent subsurface formations.

Figure 9:
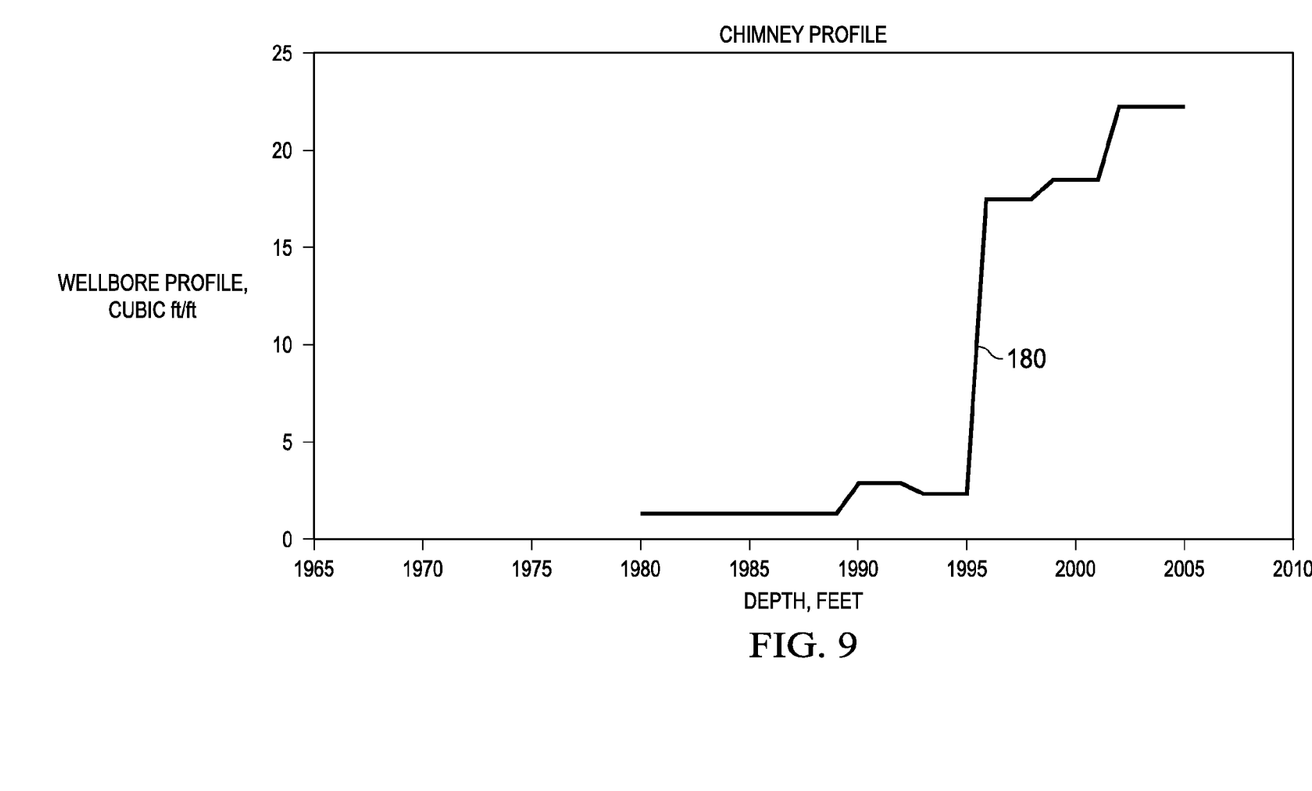
FIG. 9 is a chart illustrating a chimney profile produced in accordance with the invention.

An example of a profile, which was produced in accordance with the present invention, is shown in the chart of FIG. 9. This is the measured profile for a portion of a chimney of a storage cavern. The depth in the cavern is shown horizontally and the area in the chimney measured at various depths is shown vertically. The cavern data is plotted as line 180. The chimney area begins to increase at the depth of approximate 1990 feet. The area increases rapidly at the depth of 1995, but mostly flattens out in the range of 1997 to 2005. Line 180 represents the area profile for the top of the chimney, starting narrow and widening out. If the chimney is assumed to be cylindrical, the diameter can be calculated to an approximate value.

The above embodiments use a fixed pressure differential value to move the interface down and a measurement of gas volume to make a determination of a volume for a region of the chimney. Another embodiment is to use a fixed gas volume injection for each region with a measurement of the pressure change. This parameter exchange can be made in the above described embodiments. When these two parameters are known, the height and volume of an identified location region in the chimney are established.

A further embodiment is a bottom up measurement process, which is essentially the reverse of the above described operation. In this further embodiment, the interface 34 is initially driven to a level in the chimney 24 or in the cavern to a level in the chimney or cavern which serves as a starting level. This can be, for example, the level at line 178 in FIG. 8. This level of the interface can be set by acoustic sounding using the well analyzer 50 and gas gun 52 as described above. At this level of the interface 34 (FIG. 8), the gas pressure at the surface 12 is measured by pressure gauge 142. The gas in the annulus is then released at the surface through valves 78 and 80 until the surface gas pressure is reduced by a predetermine amount, for example, 0.33 psi. This pressure reduction allows the interface 34 to rise to the level of line 176 as shown in FIG. 7. This establishes the region 164. A further reduction of gas pressure by 0.33 psi allows the interface to rise to the level of line 174, as shown in FIG. 6 to form region 162. A still further reduction in surface gas pressure by 0.33 psi raises the gas interface 34 to the level of line 172 as shown in FIG. 5 to define region 160. The diameters of each region are calculated as described above.

Although several embodiments of the invention have been illustrated in the accompanying drawings and described in the foregoing Detailed Description, it will be understood that the invention is not limited to the embodiments disclosed, but is capable of numerous rearrangements, modifications and substitutions without departing from the scope of the invention.

What is claimed is:

1. A method for determining at least a portion of a chimney profile of a cavern which has a casing that extends from the earth surface down to the chimney and contains a hydrocarbon liquid, wherein the cross-sectional area of the chimney below the lower end of the casing is greater than that of the casing, comprising the steps of:
    (a) opening a valve for injecting a gas into said casing at the surface to drive an interface between the gas and said liquid down to a first level within said chimney,
    (b) monitoring the pressure of said gas in the casing at the surface,
    (c) determining a first gas pressure in said casing at the surface when said interface is at said first level,
    (d) after said interface has reached said first level, injecting said gas through said valve into said casing at the surface to increase the pressure of said injected gas in the casing at the surface by a difference pressure value to drive said interface down to a second level,
    (e) determining the distance between said first level and said second level based on a gradient (pressure/distance) of said liquid and said difference pressure value,
    (f) measuring the volume of said gas injected into said casing that moved said interface from said first level to said second level to determine the volume of said chimney between said first level and said second level, and
    (g) closing said valve to terminate the flow of said gas into said casing after the pressure of said gas has increased by said difference pressure value and said volume of said gas has been measured.

2. A method as recited in claim 1 wherein said gradient is determined by measurement of the density of a sample of said liquid taken from said casing.

3. A method as recited in claim 1 wherein said gradient is determined by dividing a surface casing gas pressure differential for pressures corresponding to said interface located at first and second known depth levels by the distance between the first and second known depth levels.

4. A method as recited in claim 1 wherein the following steps are repeated to measure the height and volume of additional regions below a first region which is between said first level and said second level:
    (a) inject said gas through said valve into said casing at said surface to increase the pressure of said injected gas in said casing at said surface by a further difference pressure value to drive said interface down from a previously established level to a next level,
    (b) determine the height of a next region between said previously established level and said next level based on a gradient (pressure/distance) of said liquid and said further difference pressure value, and
    (c) measure the volume of said gas injected into said casing to move said interface from said previously established level to said next level to determine the volume of said next region of said chimney.

5. A method as recited in claim 3 wherein said first known depth level is said surface and said second known depth level is a reference level located a short distance below the lower end of said casing.

6. A method as recited in claim 1 including a compensation of surface measured volume to volume in the chimney based on gas column weight and temperature.

7. A method for determining at least a portion of a chimney profile of a cavern which has a casing that extends from the earth surface down to the chimney and contains a hydrocarbon liquid, wherein the cross-sectional area of the chimney below the lower end of the casing is greater than the of the casing, comprising the steps of:
    (a) opening a valve for injecting a gas into said casing at the surface to drive an interface between the gas and said liquid down to a first level within said chimney,
    (b) monitoring the pressure of said gas in the casing at the surface,
    (c) determining a first gas pressure in said casing at the surface when said interface is at said first level,
    (d) after said interface has reached said first level, injecting through said valve a measured volume of said gas into said casing at the surface which increases the pressure of said injected gas in the casing at the surface by a first pressure value and drives said interface down to a second level, wherein said volume of said gas determines the volume of a chimney region between said first level and said second level,
    (e) determining the distance between said first level and said second level based on a gradient (pressure/distance) of said liquid and said first pressure value, and
    (f) closing said valve to terminate the flow of said gas into said casing after the pressure of said gas has increased by said first pressure value and said volume of said gas has been injected into said casing.

8. A method as recited in claim 7 wherein said gradient is determined by measurement of the density of a sample of said liquid taken from said casing.

9. A method as recited in claim 7 wherein said gradient is determined by dividing a surface casing gas pressure differential for pressures corresponding to said interface located at first and second known depth levels by the distance between the first and second known depth levels.

10. A method as recited in claim 7 wherein the following steps are repeated to establish the height and volume of additional regions below a first region which is between said first level and said second level:
  (a) inject another measured volume of said gas through said valve into said casing to drive said interface down from a previously established level to a next level, and
  (b) measure the change in pressure of said gas injected into said casing to move said interface down from said previously established level to said next level to determine the height of a next region of said chimney based on said change in pressure and said gradient of said liquid.

11. A method as recited in claim 9 wherein said first known depth level is said surface and said second known depth level is a reference level located a short distance below the lower end of said casing.

12. A method as recited in claim 7 including a compensation of surface measured volume to volume in the chimney based on gas column weight and temperature.

* * * * *